United States Patent [19]
Bowald

[11] Patent Number: 4,713,072
[45] Date of Patent: Dec. 15, 1987

[54] IMPLANT LENS AND METHOD AND APPARATUS FOR ITS PRODUCTION

[75] Inventor: Staffan F. Bowald, Storvreta, Sweden

[73] Assignee: Swedish Graft Technique AB, Sweden

[21] Appl. No.: 932,298

[22] Filed: Nov. 19, 1986

[30] Foreign Application Priority Data

Nov. 22, 1985 [SE] Sweden .................. 8505518

[51] Int. Cl.⁴ .......... A61F 2/16; A61B 17/00
[52] U.S. Cl. .................. 623/6; 128/303 R; 427/2
[58] Field of Search .................. 623/6, 4–5; 128/303 R; 427/2

[56] References Cited

U.S. PATENT DOCUMENTS

| | | | |
|---|---|---|---|
| 4,170,043 | 11/1977 | Knight et al. | 623/6 |
| 4,240,163 | 1/1979 | Galin | 623/6 |
| 4,585,457 | 4/1986 | Kalb | 623/6 |
| 4,619,662 | 10/1986 | Juergens, Jr. | 623/6 |

FOREIGN PATENT DOCUMENTS

WO85/04566 10/1985 PCT Int'l Appl. .......... 6/

*Primary Examiner*—Ronald L. Frinks
*Attorney, Agent, or Firm*—Bacon & Thomas

[57] ABSTRACT

An improved intraocular or implant lens has at least the outer layer thereof consisting of a substantially water-insoluble, biodegradable and biocompatible materila. Methods of preparing such a lens and an apparatus for carrying out such a method are also disclosed.

13 Claims, 5 Drawing Figures

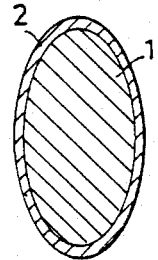
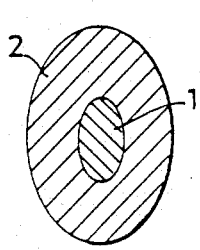
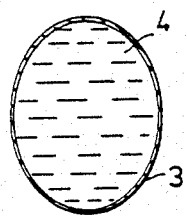
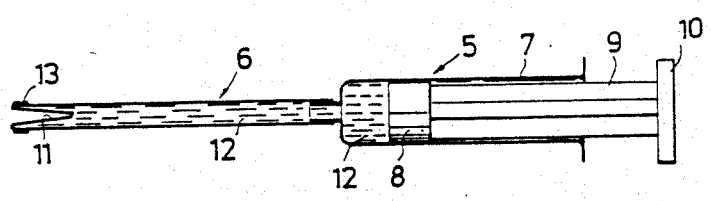
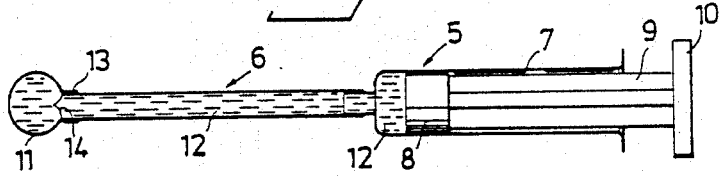

IMPLANT LENS AND METHOD AND APPARATUS FOR ITS PRODUCTION

The present invention relates to improved eye lenses intended as a substitute for the natural eye lens of human beings or animals, and more particularly to novel intraocular or implant lenses which are not subject to any opacity problems even after long-term use.

The disease cataract in its various forms causes an opacity of the eye lens which often results in such a serious impairment of the vision that the lens must be removed surgically. To compensate for the lens or lenses the patient must wear highly refracting positive glasses or contact lenses. Recently, however, it has become increasingly usual to replace the surgically removed lens by an implanted artificial lens, usually from a plastic material. Various lens designs and operative methods for the insertion and securing thereof in the eye are described in the literature.

A serious disadvantage of the hitherto used lenses has, however, been the fact that the lense materials used, although classified as biocompatible, have a slight, but not negligible, irritating effect on their environment, and usually already within a few years, the lenses start to develop various degrees of opacity due to the precipitation of fibrin and/or due to the growth of connective tissue to the artificial lens surface. When the opacity has become too extensive, the layer causing the opacity must be removed, and special techniques therefor, including the use of a laser, have been developed. Alternatively, the whole lens is replaced. The period of time that the implanted lens will function satisfactorily is therefore relatively short, and it may thus in many cases be doubtful if the replacement of the surgicially removed eye lens with any of the hitherto available intraocular lenses will cause any advantage to the patient in the long run in relation to the conventional cataract glasses or contact lenses.

It is previously known to provide artificial lenses with a coating.

U.S. Pat. No. 4,240,163 discloses the coating of an intraocular lens with a compatible medicament, such as anti-coagulant, an anti-inflammatory agent or an anti-complement agent in order to reduce damage to the corneal endothelium upon contact and upon the secondary responses of inflammatory cellular response.

U.S. Pat. No. 4,170,043 discloses an intraocular lens covered with a biocompatible water-soluble adherent film coating having a dissolution rate which maintains at least 40% of the coating on the lens for at least 30 minutes, but not more than 24 hours, when submerged in an aqueous medium simulating the surgical environment. The purpose of the cover is to protect against static and sliding contact with the corneal endothelium. Polyvinyl alcohol is an example of such a short-term initial coating, which is said to be superior to previously used coatings for the same purposes, such as methylcellulose or polyvinylpyrrolidone. Upon contact with water the polyvinyl alcohol coating hydrates to a swollen state, the outer portions of the swollen coating being sluffable during sliding contact with the corneal endothelium.

None of the lens coatings disclosed by the above cited references is, however, capable of reducing to any substantial extent or obviating the above discussed opacity problem.

It is an object of the present invention to overcome the above disadvantages of the prior art intraocular lenses. Thus, in accordance with the present inventive concept it has now surprisingly been found that the above mentioned opacity problem may be eliminated if at least the ouutermost layer of the artificial lens initially is composed of a biocompatible, substantially water-insoluble and slowly biodegradable and absorbable material, for convenience hereinafter simply called "bioresorbable material", which layer will function as a growth zone for the natural eye lens tissue. As this layer is slowly degraded and resorbed by the body, it is successively replaced by the normal lens tissue and no attaching growth of connective tissue or precipitation of fibrin with accompanying opacity phenomenons are obtained.

One aspect of the present invention therefore relates to an artificial lens member, intended to replace the surgically removed natural lens of an eye, which lens member is characterized in that it at least in the outer layer thereof consists of a bioresorbable material as defined above.

While it would be sufficient that the lens has only a relatively thin layer of the bioresorbable material to achieve the purposes of the present invention, a substantially greater part of the lens, or even the whole lens, may consist of such a material. In fact, the invention comprises lenses, in which the bioresorbable material may constitute anything from a relatively thin layer (at least, however, about 10 microns) covering a lens core of a non-resorbable material to the whole lens body.

The lens body may, within the scope of the invention, be rigid or flexible, depending upon the material or the material combination from which it is prepared. Where a combination of resorbable and non-resorbable materials are used, the non-resorbable core may be rigid and the resorbable cover soft or flexible, or vice versa, or the non-resorbable core and the resorbable cover may both be of either rigid or flexible nature.

Of course, both the resorbable and the non-resorbable materials may each, if desired, consist of two or, possibly, more different resorbable and non-resorbable materials, respectively. In case the whole lens is of bioresorbable material, it may, for example, consist of a solid, preferably flexible, cover or envelope of a first bioresorbable material which is filled with a second bioresorbable material in a flowable or liquid state, such as a gel. Such a lens design is in fact a preferred embodiment of the invention and will be described in more detail below.

The bioresorbable material of the lens may, for the purposes of the invention, be solid, but preferably it is porous, particularly microporous, to permit the passage of fluids.

While not absolutely necessary, it is, as is readily appreciated, preferred that the bioresorbable materials used, are substantially crystal-clear.

The resorption period of the bioresorbable material, which, of course, will depend, on one hand, on the particular material and, on the other hand, on the thickness or volume thereof, should be sufficient to permit the in vivo replacement thereof with the normal eye lens tissue. It would, however, generally, be at least about four weeks, and a suitable resorption period has been found to be from about 4 months to about 1 year.

Suitable bioresorbable materials for the purposes of the present invention, with regard to resorption rate characteristics etc., i.e. substantially water-insoluble and biodegradable materials which are non-toxic, have no adverse tissue reaction and upon degradation are capable of being completely resorbed in the body without giving rise to scar tissue or toxic degradation products, may readily be selected by the skilled person, e.g., among those materials which either are or will be commercially available or are described in the literature.

As examples of bioresorbable materials may be mentioned those based upon polyglycolic acid (PGA), copolymers of glycolic acid and lactic acid, and various lactide polymers. PGA-esters are, e.g., described in the U.S. Pat. No. 3,463,158. Copolymers of glycolic acid and lactic acid are, for example, described in the U.S. Pat. No. 3,982,543, while homo and copolymers of lactic acid are described, e.g., in the U.S. Pat. No. 3,636,956. Examples of commercially available materials are VICRYL ® (a copolymer of 90% glycolic acid and 10% lactic acid, marketed by Ethicon, Sommerville, N.J., U.S.A.—also known as Polyglactin 910) and DEXON ® (Davies & Geck, Pearl River, N.Y., U.S.A.). Further examples are polydesoxazon (PDS) (Ethicon, USA), polyhydroxybutyric acid (PHB), polyester of succinic acid, and cross-linked hyaluronic acid. The person skilled in the art would have no difficulty to modify such or similar bioresorbable materials as required to achieve the desired porosity, resorption time, etc.

The above mentioned preferred porosity of the bioresorbable material may be achieved in various ways, e.g., by providing it as a three-dimensional net structure, spongy structure, etc.

Another aspect of the present invention relates to the production of the inventive implant or intraocular lens.

A lens according to the invention of the type having a core of a nonresorbable material may be prepared by coating the core with the particular bioresorbable material(s) in any per se conventional manner.

A lens according to the invention of the above mentioned preferred type, consisting of an envelope of a bioresorbable material filled with a liquid, bioresorbable material, preferably in gel form—an embodiment which has great similarities with the natural eye lens—may, for example, be prepared by forming a bag-like envelope of a solid, preferably flexible, bioresorbable material, which is then filled with a liquid bioresorbable material, whereupon the envelope is sealed in any suitable manner, e.g., by heat-sealing when the envelope is of a heat-sealable material, or glueing.

When necessary, any per se conventional type fastening means for the lens, such as supporting loops, etc., may be used, which in such a case preferably are of a bioresorbable material or at least coated with such a material.

Still another aspect of the present invention is an apparatus or instrument for carrying out the above last-mentioned method. Such an instrument consists of a piston/cylinder based injection means, e.g., of the hypodermic syringe type, intended to be filled with a flowable bioresorbable material, preferably in gel form, and which, for example, via a cannular tube means, is communicatively connected to a relatively thin bag- or bubble-shaped member of a bioresorbable material providing the envelope. This bag or bubble-shaped member may be integral with a cannular tube of bioresorbable material and be formed by blowing or by an other suitable means. Alternatively, the bag or bubble-shaped end may be a separate part of bioresorbable material which is, e.g., screwed or snapped, to the cannular part which in such a case will be of a non-resorbable material.

The implant lens according to the invention is preferably applied into the incised lens sac of the eye, after the natural lens has been removed by any per se conventional surgical technique. When using the above described instrument the bubble-shaped member thereof is inserted into the incised lens sac, whereupon the polymer gel in the syringe cylinder is injected into the bag or bubble-shaped end such that the latter is filled up. The filled envelope is then removed and sealed; when integral with the tube it may be cut off in any suitable way and sealed to enclose the gel material, e.g., by heat-sealing or glueing, which may be effected by suitable means which preferably are integral with the instrument. When forming a separate part the envelope member may suitably be provided with some kind of non-return valve means. The same type of instrument may, of course, also be used for producing and inserting an intraocular lens completely of non-resorbable materials, i.e. the envelope as well as the fluid filler.

Hereinafter the invention will be described in more detail with respect to some particular non-limiting embodiments, reference being made to the accompanying drawings, wherein:

FIGS. 1A and 1B are variations of one embodiment of an implant lens according to the present invention;

FIG. 2 is another embodiment of an implant lens according to the present invention;

FIG. 3 is a schematic illustration of an instrument according to the present invention for producing an implant lens according to FIG. 2; and FIG. 4 is a corresponding view as FIG. 3 but showing the instrument after the lens envelope has been filled with a gel material.

The lens embodiments of FIGS. 1 and 2 consist of a core 1 of a material which is not resorbed in the body and provided with a cover 2 of a bioresorbable material as defined above. FIG. 1A illustrates a relatively thin cover 2, while FIG. 1B shows a reduced core 1 and a thicker cover 2. The non-resorbable core 1 may, for example, consist of any material which is conventionally used for intraocular or implant lenses, such as polymethacrylic ester, e.g., polymethylmethacrylate, polyamide, silicone, etc., or any other suitable non-resorbable biocompatible material. The bioresorbable material of the envelope 2, may for example, be Polyglactin 910 (Vicryl ®, Ethicon, U.S.A.) or any other substantially water-insoluble, biodegradable and biocompatible material. The proportions between the core 1 and the envelope 2 may, of course, be varied in relation to those shown, and the bioresorbable cover 2 may possibly only consist of a thin coating on the surface of the core 1. The bioresorbable material 2 is preferably microporous, such that the body fluids may penetrate.

The embodiment illustrated in FIG. 2 is completely composed of bioresorbable materials and comprises a relatively thin shell or envelope 3 of a first bioresorbable material, filled with a second flowable bioresorbable material 4, preferably in gel form.

The envelope 3 may, for example, like the embodiment of FIG. 1, consist of Polyglactin 910 (Vicryl ®), while the gel contents 4, e.g., may be cross-linked hyaluronic acid.

The embodiment of FIGS. 1A and B is an example of a "hard" lens, provided that the core 1 is relatively rigid, while the embodiment according to FIG. 2 is an example of a "soft" lens. Depending on the materials used the embodiment of FIG. 1 may, of course, also be effected as a soft lens.

When implanting the embodiments illustrated in FIGS. 1A and B and 2 into the eye the natural lens is removed in conventional manner by opening the lens capsule sac and removing the natural lens. The lens member of the invention is then inserted into the lens capsule sac. After some time, depending upon the particular bioresorbable material(s) used and the lens design, the bioresorbable material has completely been replaced with natural lens tissue, e.g., within a period of about 4 months to 1 year depending upon the bioresorbable material used, the thickness thereof, etc.

FIGS. 3 and 4 schematically show an instrument for forming and inserting the lens according to FIG. 2 into the lens capsule sac. The illustrated instrument comprises a syringe member 5 provided with a tubular cannular-like member 6. The syringe member 5 comprises in conventional manner a cylinder 7 having a movable piston 8 therein connected to an operating rod 9 provided with a push portion 10. The tubular member 6 is, in the illustrated case, removable and consists of a bioresorbable material, e.g., Polyglactin 910 (Vicryl ®). The free end of the tube 6 has been shaped, for example, by blowing, into a relatively thin bag or bubble 11, which in FIG. 3 is shown inserted into the tube 6. The lower part of the syringe cylinder 7 is filled with a bioresorbable material 12 in gel form, e.g., cross-linked hyaluronic acid, which in FIGS. 3 and 4 has been pressed into the tube 6 by means of the piston 8.

To perform the implant operation additional gel material 12 is pressed into the tube 6, such that the bag 11 is filled out, as is shown in FIG. 4. The now filled bag 11 is then introduced into the opened lens capsule sac of the eye, whereupon the bag portion in any suitable manner is cut-off from the tube 6 and sealed to completely enclose the gel material 12. This cutting/sealing operation may conveniently be effected by suitable means which are integral with the instrument, e.g., a combination of a lacing and heat-sealing wire or the like, indicated in FIGS. 3 and 4 by reference numeral 13.

Alternatively, the bag or bubble shaped end part 11 of the tube 6 may be a separate member, which is removable attached to the tube 6 by any suitably means (not shown), e.g. by screwing or snapping. In such as case a non-return or check valve means or the like (indicated in FIG. 4 by reference numeral 14) is preferably provided to retain the gel material 12 in the removed bag or bubble member 11.

Below two experiments will be described, wherein intraocular lenses according to the invention were implanted into two experimental animals.

EXAMPLE 1

The lens of an anesthetized eye of an experimental dog was prepared in per se conventional manner, such that the contents thereof were evacuated and only the empty lens sac remained. In the empty lens sac filaments of 0.5–2 mm length and about 2–4μ thickness of Polyglactin 910 (Vicryl ®, Ethicon, Sommerville, N.J., U.S.A.) were implanted. The filaments were positioned such that they substantially lined the inside of the lens sac, while the central space was left free. Finally the shape of the lens was restored with haluronic acid in gel form (Healon ®, Pharmacia AB, Uppsala, Sweden). The polyglactin filaments then formed a very close-meshed net surrounding a half-liquid central core of hyaluronic acid. The incision of the eye was sealed with Vicryl ® suture.

During the first two weeks the lens opacified somewhat but successively cleared again during the following four weeks. After two months the lens was completely clear, refracting and had accommodation capability.

After six months the animal was killed, and the eye was removed for histologic analysis. In this analysis it was found that the natural lens had been completely reformed and only insignificant signs indicating that something had happened to the lens could be observed.

EXAMPLE 2

Filaments of Polyglactin 910 (Vicryl ®, Ethicon, Sommerville, N.J., U.S.A.) were fused together such that a lens-shaped solid unit having the size of a rabbit eye lens and a slightly irregular surface was formed.

The eye lens of a rabbit was evacuated in the same way as in Example 1, and the lens-shaped unit of Polyglactin 910 produced was inserted into the lens sac which was then sealed with Vicryl ® suture. During the first weeks after the surgical operation a certain opacity of the implanted lens was observed. The lens cleared, however, successively during the following three weeks to be completely clear and refracting after six weeks from the operation. The histologic analysis revealed that the natural lens had been completely reformed.

The invention is, of course, not restricted to the embodiments particularly described above and shown in the drawing, but many modifications can be made without departing from the spirit and scope of the invention.

What is claimed is:

1. An implant lens having at least the outer layer thereof consisting of substantially water-insoluble biodegradable and biocompatible material capable of providing a growth zone for the natural eye lens tissue.

2. A lens according to claim 1, wherein the lens comprises a lens core of a transparent, non-resorbable material.

3. A lens according to claim 2, wherein said lens core constitutes the major part of the lens and is covered by a layer of said biodegradable material.

4. A lens according to claim 1, wherein the lens entirely consists of biodegradable material.

5. A lens according to claim 4, wherein the lens comprises an envelope of a first, substantially water-insoluble solid biodegradable material enclosing a second, fluid biodegradable material.

6. A lens according to claim 5, wherein said second biodegradable material is in gel form.

7. A lens according to claim 1, wherein the biodegradable material at least in the outer part of the lens is porous.

8. A lens according to claim 1, wherein the biodegradable material at least in the outer part of the lens is microporous.

9. A lens according to claim 1, wherein the resorption period of the biodegradable material thereof is at least about four weeks.

10. A lens according to claim 9, wherein said resorption period is from about four months to about one year.

11. A method of producing an implant lens, comprising the steps of providing a lens core of a solid transparent, non-resorbable material with a cover of a substantially water-insoluble, biodegradable and biocompatible material.

12. A method of producing an implant lens, comprising the steps of providing an envelope of a first, substantially water-insoluble, biodegradable and biocompatible material, and filling it with a second biodegradable material in fluid form, and then sealing said envelope.

13. An apparatus for producing an implant lens, comprising syringe member for holding a first, fluid lens material, an envelope member of a second lens material, communicatively connected to said syringe member, and means for permitting separation of said envelope member after it has been filled with said first material to form said implant lens wherein said first and second lens materials are biodegradable.

* * * * *